(12) United States Patent
Nattkemper et al.

(10) Patent No.: US 7,382,909 B1
(45) Date of Patent: Jun. 3, 2008

(54) METHOD FOR THE AUTOMATIC ANALYSIS OF MICROSCOPE IMAGES

(75) Inventors: Tim Wilhelm Nattkemper, Bielefeld (DE); Helge Ritter, Bielefeld (DE); Walter Schubert, Biederitz (DE)

(73) Assignee: MPB MelTec Patent-und Beteiligungsgesellschaft mbH, Magdeburg (DE)

( * ) Notice: Subject to any disclaimer, the term of this patent is extended or adjusted under 35 U.S.C. 154(b) by 619 days.

(21) Appl. No.: 09/869,638

(22) PCT Filed: Nov. 3, 2000

(86) PCT No.: PCT/EP00/10833

§ 371 (c)(1),
(2), (4) Date: Feb. 8, 2002

(87) PCT Pub. No.: WO01/36939

PCT Pub. Date: May 25, 2001

(30) Foreign Application Priority Data

Nov. 4, 1999 (DE) ................................ 199 53 181

(51) Int. Cl.
*G06K 9/00* (2006.01)
(52) U.S. Cl. ....................... 382/133; 382/159; 382/224
(58) Field of Classification Search ................ 382/133, 382/159, 203, 218, 225, 291; 377/10
See application file for complete search history.

(56) References Cited

U.S. PATENT DOCUMENTS

| | | | |
|---|---|---|---|
| 5,181,259 A | 1/1993 | Rorvig | |
| 5,245,672 A | 9/1993 | Wilson et al. | |
| 5,257,182 A * | 10/1993 | Luck et al. | 382/224 |
| 5,287,272 A | 2/1994 | Rutenberg et al. | |
| 5,522,015 A * | 5/1996 | Watanabe | 706/25 |
| 5,733,721 A * | 3/1998 | Hemstreet et al. | 435/6 |
| 5,741,648 A | 4/1998 | Hemstreet, III et al. | |
| 6,221,592 B1 * | 4/2001 | Schwartz et al. | 435/6 |

FOREIGN PATENT DOCUMENTS

| | | |
|---|---|---|
| GB | 2 320 352 A | 6/1998 |
| WO | WO 97/37327 | 10/1997 |

OTHER PUBLICATIONS

Watkin, "Minimum Distance Processor for Biological Tissues Classification from A-Scan Ultrasonic Signals", IEEE 1995.*

* cited by examiner

*Primary Examiner*—Bhavesh M. Mehta
*Assistant Examiner*—Charles Kim
(74) *Attorney, Agent, or Firm*—Weingarten, Schurgin, Gagnebin & Lebovici LLP

(57) ABSTRACT

The invention relates to a method for the automatic analysis of microscope images of biological objects such as, for example, fluorescence images of cells, comprising: a) at least two microscope images are taken from a sample; b) a positive training set is determined from image excerpts; c) a negative training set is determined from a sequence of image excerpts; d) characteristic features of a training set are assigned to classification values; e) classification values of a sequence of images are automatically determined by means of the assignment determined in d); f) the position of biological objects is recognized by comparing the classification value with a threshold value.

10 Claims, No Drawings

METHOD FOR THE AUTOMATIC ANALYSIS OF MICROSCOPE IMAGES

FIELD OF THE INVENTION

The invention relates to a method for the automatic analysis of microscope images of biological objects, in particular for the analysis of fluorescence images of cells.

BACKGROUND

In numerous experiments in the field of modern biomedical research, fluorescence techniques, amongst others, are used for marking in order to make biologically significant objects visible under the microscope. Such objects may be cells of a certain type or of a certain state, for example. In recent years, the progress made in automating such experiments has made it possible for biomedical laboratories to perform large numbers of such image-producing experiments fully automatically.

DE 197 09 348 C1, for example, describes a fluorescence microscope technique which produces a set of n images of a single sample by preparing said lymphocyte sample with n different fluorochrome markers. In each image, different lymphocyte subsets will be fluorescent and appear to have shining outlines. Each lymphocyte in the sample will have its specific fluorescent behavior in the image set. It will appear fluorescent in one subset of images, otherwise remaining invisible in the other images of the set.

For extracting the fluorescence patterns from the image set, the fluorescent lymphocytes will first of all have to be detected in the n images. The fluorochrome marked lymphocytes differ in number, location and intensity. Since such vast numbers of images and image data will result, from which the information will first of all have to be extracted for biological interpretation later on, there will be a so-called bottleneck in the evaluation of the experiments. Image interpretation by human employees is impractical since it is too time-consuming and the results are often not reliable. This is due to the visual evaluation work which is tiring and will lead to concentration losses already after a short time only. Moreover, the objects to be detected differ in number, location and intensity. Consequently, image parameters such as contrast and noise will differ from image to image. Furthermore, the objects, for example cells in tissue samples, vary considerably as regards their shape and size.

Consequently, there is a need for automatic evaluation methods which are capable of locating the objects to be detected in one image.

Earlier work on the automation of cell detection essentially focused on model-based approaches. Numbering amongst these is also the idea to adapt a geometric model to a gradient ensemble (Mardia et al., 1997, In: IEEE Transactions of Pattern Analysis and Machine Intelligence, 19: 1035-1042). This also includes the exploitation of wave propagation (Hanahara and Hiyane, 1990, In: Machine Visions and Applications, 3: 97-111) or a Hough transformation for detecting circular objects (Gerig and Klein, 1986, In: Proc. Int. Conf. on Pattern Recognition, 8: 498-500). These approaches, however, have the disadvantage that they are frequently susceptible to changes in the shape of the object, and they may not be readily adapted by persons not skilled in the art. Furthermore, the images will not infrequently contain noise, owing to heterogeneous lighting conditions, and the cells will be partly obscure, which makes detection by boundary scanning unsuitable (Galbraith et al.; 1991, In: Cytometry, 12: 579-596).

SUMMARY

It is therefore the object of the present invention to provide a method of the aforementioned kind comprising a simple automatic cell detection procedure which is fast and readily adapted.

This object is accomplished by a method having the features set out in claim 1.

Advantageous embodiments are described in the subclaims.

DETAILED DESCRIPTION

The present invention relates to a method for the automatic analysis of microscope images of biological objects, in particular for the analysis of fluorescence images of cells, comprising the following steps: a) at least two microscope images are taken of a sample containing a plurality of biological objects; b) a first microscope image is selected and the positions of mass gravity centers of a number n of the individual objects visible in said first microscope image are marked, in which process each marked object is assigned a defined first image excerpt completely surrounding the marked object, and in which each first image excerpt containing a marked object is assigned the value 1, with the number n of such marked first image excerpts constituting a positive training set; c) a number m of second image excerpts which are spaced a predetermined minimum distance from the first image excerpts are selected and marked, with the size and shape of a second image excerpt corresponding to the size and shape of a first image excerpt, in which process each second image K excerpt is assigned the value 0, with the number m of such marked second image excerpts constituting a negative training set; d) characteristic features and/or feature combinations of the positive and negative training sets are determined and assigned to a classification value between 0 and 1, said classification value representing the degree of probability of the presence of a marked object, and the determined features and/or feature combinations are stored; e) classification values of all image points of the second and each further microscope image are automatically determined by comparing the image data of the second and each further microscope image with the features and/or feature combinations determined in procedural step d), in which process the classification value for an image excerpt surrounding the image point is determined for each image point of the second and each further microscope image, said image excerpt corresponding in size and shape to said first or second image excerpt; and f) the position(s) of biological objects in the second or each further microscope image is/are recognized by evaluating classification values, said determined classification values being then compared with a predetermined threshold value which represents the presence of a biological object.

The method of the invention for detecting biological objects such as cells in microscope images advantageously uses classification values which will assign to image excerpts of given size and shape a value between 0 and 1 and which will indicate whether (1) or not (0) a biological object can be seen in this image excerpt. However, it is also possible to use any other numerical values which are different from each other. In an image, all cells are found by assigning all image areas to one classification value. A simple automatic search for high values (threshold value analysis) will thus allow the positions of the biological objects to be located automatically and stored in a file and processed further, for example. Providing such classification values, or a similar classifier, and simply adapting them in case of significant changes in the microscope images due to microscope modifications, different samples, different fluorescence markers or different cell types is made possible by the use of the method of the invention which constitutes an artificial neural network.

The method of the invention will allow a fully automatic detection of biological objects such as cells in microscope images, after it has been trained by a user by being provided with a set of cell-positive image excerpts. It is particularly easy to use since it merely requires the user to mark cells on the screen for training, which is a routine activity in laboratory work. The system is thus suitable for the fast evaluation of numerous microscope images for localizing cells. Owing to its ease of use, the method of the invention can be readily applied and executed. It is suitable for supporting any kind of empirical work with microscope images of biological objects at universities as well as in industry—which sectors have a vast throughput of samples and require objective and reproducible evaluations.

In a further advantageous embodiment of the method of the invention, the sample is a tissue sample and the biological object is a cell. In particular for automatic cell detection, the method of the invention has shown to be advantageous over conventional methods of the prior art.

In yet another advantageous embodiment of the method of the invention, the biological objects to be determined are marked with one or plural chemical markers before the microscope images are taken. In this process, a bleaching or rinsing operation may be performed between the taking of the individual microscope images. The chemical markers may be fluorochrome markers and the microscope images may be fluorescence images.

For example, fluorochrome markers are used on lymphocytes in order to determine the presence of proteins in lymphocyte cell surfaces. Each marker will bind to a lymphocyte subset which depends on the existence of the respective protein in the lymphocyte surface membrane. Fluorescence excitation will cause the binding lymphocytes to appear with high intensities. A corresponding microscope image will be taken by a CCD camera. The marker will subsequently be removed from the cells by means of bleach, and the operation will be repeated using a different marker. In the embodiment described here the process comprising marking, image generation and bleaching can be repeated with up to nine markers. During each repetition, the lymphocyte positions will remain unchanged, which allows a matching or coincidence comparison of the positions in the different images. This experimental setup is especially used for analyzing T lymphocytes which have invaded the muscular tissue in a clinical case of sarcoidosis. The lymphocytes were prepared with n=7 markers, and seven fluorescence images were taken, in which different subsets of the cells appeared fluorescent. On conclusion of all n steps, a set of n microscope images with different lymphocyte subsets can be evaluated. The n microscope images are evaluated by means of the method of the invention.

In this case, the number n of the individual biological objects, in particular cells, marked in procedural step b) will be larger than or equal to 50. For each marked point, it will be decided whether or not such point constitutes a cell center. Since the lymphocytes, for example, will be in organic fiber material during an invasion situation, they will not be circular in shape, but irregularly oblong, which shape is referred to as predominantly convex. For the classification of the biological objects, a special form of a neural network, the so-called "Local Linear Map" (LLM) (Ritter, 1991: In: Artificial Neural Networks, Elsevier Science Publishers B.V.) is used. The LLM classifier is trained by a set of image excerpts which contain cells. For training the LLM classifier, according to procedural step b) an image is selected from the image set. Furthermore, e.g. by means of a computer mouse, a group of fluorescing cells are marked. The group of image excerpts dimensioned N×N surrounding these cells will constitute the set of positive training examples or a positive training set. The first image excerpt is square in shape, according to an advantageous embodiment of the method of the invention, with the size N×N or the side length N of the first image excerpt corresponding to the maximum diameter of the biological objects in the first microscope image.

A further set of second image excerpts is randomly selected fully automatically from the same image, according to procedural step c), thereby keeping a minimum distance of e.g. 3-5 pixels from the already marked first image excerpts. This second set constitutes the set of negative training examples or a negative training set. According to an advantageous embodiment of the invention, the number m of second image excerpts will be larger than or equal to 50, with the second image excerpts being defined automatically, at the same time keeping to the minimum distance from the respective first image excerpts.

In an embodiment, a $d_{in}$ dimensional feature vector x will be calculated for each training example excerpt. The set of selected image excerpts will be subjected to a principal component analysis (PCA). This is a known technique for classification tasks in computer vision. The basic idea of PCA is that the high-dimensional image excerpt is mapped to a considerably smaller dimensional ($d_{in}$=approx. 6) feature space. These features will give so-called input feature vectors x. The feature vectors have clearly less data than the actual image excerpts. Calculation of the feature vectors for the positive and negative input examples will result in the training set of the (input, output) pair $$\Gamma=\{(x_\alpha,y_\alpha)\}_\alpha.$$

For the positive training set, $y_\alpha$ will be set to equal 1, and to equal 0 for the negative ones.

The LLM is defined by
$\{w_i^{in} \in R^{d_{in}}, w_i^{out} \in R^{d_{out}}; A_i \in R^{d_{in} \times d_{out}}, i=1 \ldots 1\}$.

A triple $v_i=(w_i^{in}, w_i^{out}, A_i)$ is referred to as a node. For training the LLM, a pair $(x_\alpha, y_\alpha)$ is randomly selected from $\Gamma$, and the learning rules $$\Delta w_k^{in} = \epsilon^{in}(x_\alpha - w_k^{in}) \qquad (1)$$

$$\Delta w_k^{out} = \epsilon^{out}(y_\alpha - y(x_\alpha)) + A_k \Delta w_k^{in} \qquad (2)$$

$$\Delta A_k = \epsilon^A (y_\alpha - y(x_\alpha)) \frac{(x_\alpha - w_k^{in})^T}{\|x_a - w_k^{in}\|^2} \qquad (3)$$

will be implemented. $\epsilon^{in}, \epsilon_{out}, \epsilon^A \subset ]0,1[$ are descending learning step sizes and k is true for k=arg $\min_k\{\|x - w_k^{in}\|\}$. Therefore, $w_k^{in}$ is the nearest neighbor to input x. This is repeated 1*10,000 times.

The trained LLM classifier performs a mapping of fluorescence image points to classification or evidence values in (0;1). For calculating the classification value for e.g. a fluorescent cell at an image point, the feature vector x for its surrounding area will be calculated. The LLM output for the input x is calculated by $$y(X) = w_k^{out} \times A_k(x - w_k^{in}) \text{ with } k = \arg\min_k\{\mu x - w_k^{in}\|\} \qquad (4)$$

In the embodiment described, the number of nodes is i=5, and the image excerpt size is N=15 pixels.

For the detection of all biological objects, e.g. fluorescent cells, in the second or each further image of the image set, each image point is mapped to its classification value by equation (4). The surrounding image region of the point will be supplied to the classifier which will then calculate its classification value. By calculating the classification values for each point in an image, a so-called classification or evidence map of the image will be obtained. Regions of high classification values or evidences will indicate biological objects such as fluorescent cells in the fluorescence image in question. All points of a classification value higher than e.g. 0.5 and without major evidences in their vicinity will form the set of positions of biological objects such as fluorescent cells in the image. A similar approach will be adopted for all further microscope images of the image set.

In accordance with an advantageous embodiment of the invention, the classification values of all image points of the second and each further microscope image are determined automatically according to procedural step e) by scanning the image surface of the second and each further microscope image.

In another advantageous embodiment of the method of the invention, the object positions determined by the procedural steps a) to f) are compared in the totality of the microscope images—which will determine the spatial position and the distribution of the individual objects in the sample.

This will allow fluorescence patterns of cells, for example, to be determined. In doing so, after the cell detection process in all images, locally corresponding fluorescence sites are found in different images so as to map fluorescences of the same cell to its marker combination pattern. This coincidence analysis is exclusively based on the positions of the cells in the images, and is a difficult task since the determined positions of one and the same cell will not always be exactly identical in different images. Furthermore, the number of fluorescent cells in the images will vary strongly. Both aspects make a simple matching on the basis of exclusively the detected cell positions impossible. The method of the invention avoids such problems by evaluating the classification values or evidences of all images of the image set.

By determining the classification values or evidences of all n images as described above, one will obtain n classification or evidence values for each point. Subsequently, the maximum evidence value for each point will be selected and entered into a new evidence map at its coordinates. This map is referred to as "Master Evidence Map" since each biological object, for example a cell, which occurred in at least one of the images, will be represented by a high evidence value in this map. Applying procedural step f) to said "Master Evidence Map" will result in all positions of the biological objects. This set of M cell positions $\{(x_i, y_i)\}$ is referred to as the "master set". Subsequently, the binary fluorescence values $f_j^{(i)}$ will be collected for each biological object from the "master set". $f_j$ of $p_i=(f_1^{(i)}, \ldots, f_n^{(i)})$ will be set to 1 when a biological object such as a cell in the j-th fluorescence image of the image set was detected in close vicinity to its coordinates $(x_i, y_i)$. A simple local matching procedure between the master set and the classification values of the positions of the biological objects, or cell positions, detected for all fluorescence images will give the binary fluorescence patterns of all detected objects or cells.

One use, according to the invention, of the described new method for the automatic analysis of microscope images of biological objects is the automatic cell classification of fluorescent cells. For example, a set of seven fluorescence images was taken according to the method of the invention. The seven different markers are cd2, cd3, cd4, cd8, cd11b, cd19 and cd26; these are antibody markers commonly used in fluorescence microscopy. The training set of all cell excerpts was selected by hand, from the cd4 image, to be precise. In each image, the fluorescent cells were detected by means of the LLM classifier. Using the maximum condition of the classification values or evidences calculated by the LLM, the "Master Evidence Map" was generated. The positions of M=550 fluorescent cells were then extracted from said "Master Evidence Map". Finally, the local matching step produced the marker combination pattern $p_j$, j=1, . . . , 550.

For examining the distribution of the marker combination patterns within the lymphocyte group, their binary patterns $(f_1^{(i)}, \ldots, f_7^{(i)})$ were mapped from the dual system to a numerical label in the decimal system. The pattern frequencies were counted and illustrated in the form of a histogram (histogram including $2^7$=128 bars). This has shown that only 24 of 128 possible patterns in the total lymphocyte group were found. Three patterns dominate in number, (1000000) (=1), (0010000) (=8) and (1010000) (=9). These are cells which bound to only cd2 or cd4, or to both these markers only. The remaining frequencies are below 30.

In order to get an idea of the coincidence of a certain marker compared to the remaining markers, a corresponding histogram was calculated for each marker. The absolute number of cells which were made fluorescent by this selected marker were shown. It was possible to determine that the absolute number of fluorescent cells will vary strongly. Most dominant are the markers cd2 and cd4. Lymphocytes fluorescence-marked with cd19 occur seldom and only once coincide with another marker (cd2). This means that this marker is highly selective. A strong coincidence may also be observed for example between the pairs (cd2, cd8), (cd3, cd8) and (cd2, cd3).

In the embodiment described, microscope images of a single visual field were recorded and analyzed. However, if one is confronted with an enormous number of several hundred visual images, for example, then the method of the invention will allow a precise statistical analysis of those immune cell subsets which have penetrated the tissue sites, within a relatively short time.

What is claimed is:

1. A method for the automatic analysis of microscope images of biological objects, in particular for the analysis of fluorescence images of cells, comprising the following steps:
   a) taking at least two microscope images of a sample including a plurality of biological objects;
   b) selecting a first microscope image and marking the positions) of mass gravity centers of a number n of the individual objects discernible in the first microscope image, in which step each marked object is assigned a defined first image excerpt which completely surrounds the marked object, and each first image excerpt including a marked object is assigned the value 1, with the number n of such marked first image excerpts constituting a positive training set;
   c) selecting and marking a number m of second image excerpts in said first microscope image each spaced a predetermined minimum distance from said first image excerpts, with a second image excerpt corresponding in size and shape to said first image excerpt, in which step each second image excerpt is assigned the value 0, with the number m of such marked second image excerpts constituting a negative training set;

d) determine characteristic features and/or feature combinations of the positive and negative training sets and assigning said characteristic features and/or feature combinations to a classification value between 0 and 1, said classification value representing the degree of probability of the presence of a marked object, and the determined features and/or feature combinations are stored;

e) determine classification values of all image points of the second and each further microscope image by comparing the image data of the second and each further microscope image with the features and/or feature combinations in said first microscope image determined in procedural step d), in which step, for each image point of the second and each further microscope image, the classification value for an image excerpt surrounding the image point is determined and the size and shape of this image excerpt corresponds to the size and shape of the first or second image excerpt; and f) recognizing the position(s) of biological objects in the second or each further microscope image by evaluating the determined classification values, in which step the determined classification values are compared with a given threshold value representing the presence of a biological object, wherein classification values of all image points of the second and each further microscope image are automatically determined according to procedural step e) by scanning the image surface of the second and each further microscope image and wherein, further, the object positions determined by procedural steps a) to f) are compared in the total number of microscope images so as to obtain a spatial location and distribution of the individual objects in the sample; wherein the position(s) of the biological objects are obtained by determining the maximum value of the classification values determined for each corresponding point in the at least two microscope images; wherein the biological objects to be determined are marked with a different set of one or plural chemical markers before each microscope image is taken, and a bleaching or rinsing procedure is performed between taking an image and taking the next image; and wherein at least one said bleaching procedure is performed.

2. The method as claimed in claim 1 wherein the sample is a tissue sample and the biological object is a cell.

3. The method as claimed in claim 1 wherein said chemical markers are fluorochrome markers and the microscope images are fluorescence images.

4. The method as claimed in claim 1 wherein the microscope images are taken by a CCD camera and then digitized.

5. The method as claimed in claim 1 wherein the number n of the individual biological objects marked in procedural step b) is larger than or equal to 50.

6. The method as claimed in claim 1 wherein the first image excerpt is of square shape, with the size and/or side length of the first image excerpt corresponding at least to the maximum diameter of the biological objects in the first microscope image.

7. The method as claimed in claim 1 wherein the number m of second image excerpts is larger than or equal to 50, with the second image excerpts being defined automatically, keeping to the minimum distance from the respective first image excerpts.

8. The method as claimed in claim 1 wherein the threshold value of the classification value representing the presence of a biological object is at least 0.5.

9. A method as claimed in claim 1 wherein fluorescent cells in said sample are automatically classified.

10. The method as claimed in claim 1 wherein said chemical markers are fluorochrome markers and the microscope images are fluorescence images.

* * * * *

UNITED STATES PATENT AND TRADEMARK OFFICE
CERTIFICATE OF CORRECTION

PATENT NO. : 7,382,909 B1
APPLICATION NO. : 09/869638
DATED : June 3, 2008
INVENTOR(S) : Tim Wilhelm Nattkemper et al.

It is certified that error appears in the above-identified patent and that said Letters Patent is hereby corrected as shown below:

Column 2, line 32, "K" should be deleted;

Column 4, line 56, "$\epsilon_{out}$" should read --$\epsilon^{out}$--; and

Column 4, line 67, "$\{ux\text{-}w_k^{in}\|\|\}$" should read --$\{\|x\text{-}w_k^{in}\|\|\}$--.

Signed and Sealed this

Twenty-seventh Day of October, 2009

David J. Kappos
*Director of the United States Patent and Trademark Office*